United States Patent [19]

Yelland et al.

[11] Patent Number: 5,010,192

[45] Date of Patent: Apr. 23, 1991

[54] PYRIDAZINONE MANUFACTURE

[75] Inventors: Michael Yelland, Rossendale; John Conway, Manchester, both of England

[73] Assignee: Imperial Chemical Industries PLC, London, England

[21] Appl. No.: 406,338

[22] Filed: Sep. 13, 1989

[30] Foreign Application Priority Data

Sep. 13, 1988 [GB] United Kingdom ............... 8821449

[51] Int. Cl.$^5$ ..................................... C07D 237/24
[52] U.S. Cl. ................................................ 544/239
[58] Field of Search ..................................... 544/239

[56] References Cited

U.S. PATENT DOCUMENTS

| | | | |
|---|---|---|---|
| 4,345,934 | 8/1982 | Fujimoto | 544/239 |
| 4,623,378 | 11/1986 | Dürr et al. | 544/239 |
| 4,732,603 | 3/1988 | Patterson | 544/239 |

OTHER PUBLICATIONS

Patterson, Chem. Abst. 97-92301c (1982), EP 49,971.

*Primary Examiner*—Cecilia Shen
*Attorney, Agent, or Firm*—Cushman, Darby & Cushman

[57] ABSTRACT

Improved method for the manufacture of plant regulant pyridazine-4-one carboxylic acids, which comprises the step of decarboxylating a 4-oxo-3, 5-pyridazine dicarboxylic acid to give a 4-oxo-5-pyridazine carboxylic acid by treatment with 95–100% sulphuric acid at 160°–180° C. using a reactant; acid weight ratio of about 1:4 to 1:10.

4 Claims, No Drawings

PYRIDAZINONE MANUFACTURE

This invention relates to pyridazinone manufacture, and more particularly to the manufacture of 4-pyridazinone carboxylic acids of formula (I):

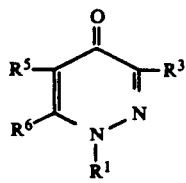

where: $R^1$ is a phenyl group, optionally substituted with, e.g. alkyl or halo groups, $R^3$ is H, alkyl or halo; $R^5$ is a carboxy group or a derivative thereof; $R^6$ is H, alkyl or halo.

Compounds of formula (I) are useful as plant growth regulating compounds, and in particular as chemical hybridising agents. They have found use as male sterilants for cereal crops, for example wheat and barley, and are useful for making hybrids in such crops.

It is known from European Patent Application No. 49971 to manufacture compounds of the above formula according to the following reaction scheme.

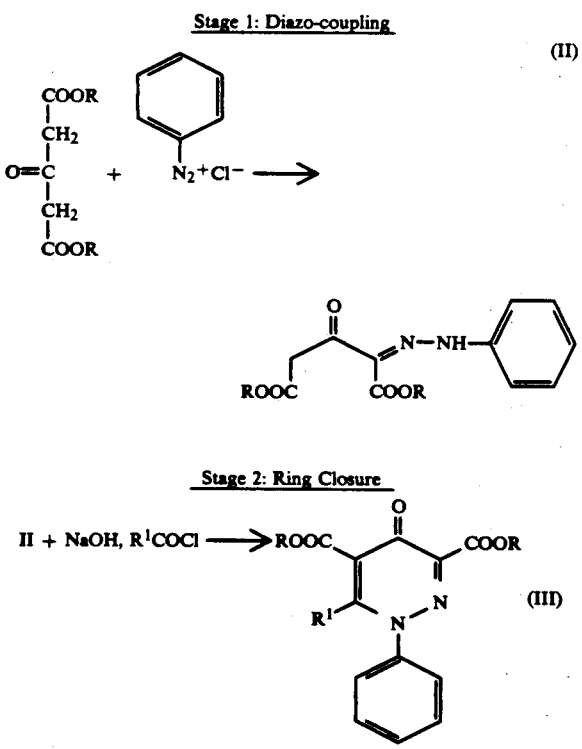

The compound (III) so obtained may then be hydrolysed either partially to the mono ester or completely to the dicarboxylic acid; and the resulting dicarboxylic acid may be partially decarboxylated. This generally gives a mixture of the two possible monocarboxylic acids, from which the desired product may be recovered.

We have now devised an improved decarboxylation step, from which the desired 5-carboxylic acid may be economically recovered in good yield and with high purity.

According to the present invention we provide a process for recovering a monocarboxylic acid of formula (V):

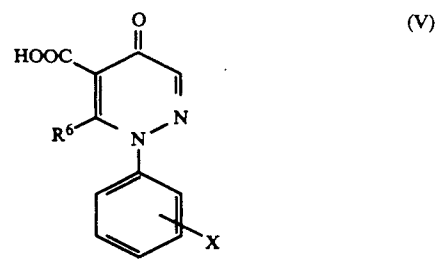

from a dicarboxylic acid of formula (IV):

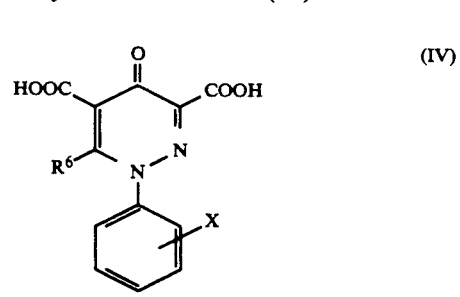

where $R^6$ is H, alkyl or halo, and X represents hydrogen or from one to three substituents (which may be the same or different) selected from alkyl, halo or nitro; which comprises heating the compound (IV) at a temperature in the range 160°–180° C. with 95–100% sulphuric acid for a time sufficient to bring about substantial monodecarboxylation, the weight ratio of (IV) to sulphuric acid used being in the range from about 1:4 to about 1:10.

By "100% sulphuric acid" we understand material corresponding to the molecular formula $H_2SO_4.H_2O$. "95% sulphuric acid" then corresponds to material containing 95% by weight $H_2SO_4.H_2O$ and 5% by weight additional water. Oleum may be made from 100% sulphuric acid by the addition of sulphur trioxide: use of this material does not form part of our invention, as it tends to produce undesired sulphonated by-products.

Reaction according to our invention is usually complete in six to seven hours, though shorter or longer times (e.g. 1 hour, 24 hours) may sometimes be found appropriate. The products of our invention are obtained in good yield, e.g. 70% theoretical or greater, and often in high purity (95% or better). We particularly prefer to use sulphuric acid of about 98% concentration, and in a reactant: acid ratio of between 1:5 and 1:8.

$R^6$ in our invention is preferably $C_1$–$C_6$ alkyl, particularly methyl or ethyl: X is preferably monochloro, particularly p-chloro. The dicarboxylic acid used as a starting material may be made, for example, by the processes described in European Patent Application No. 49971, or by the process disclosed in our co-pending application of even date herewith (claiming priority from UK Patent Appln No. 8821448.1). For use as a plant growth regulant, the products of our invention are conveniently converted to sodium or potassium salts by treatment with alkali.

The following Examples illustrate the invention.

EXAMPLE 1

Preparation of 4-oxo-1-p-chlorophenyl-6-ethylpyridazine-5-carboxylic acid (VA)

Scheme

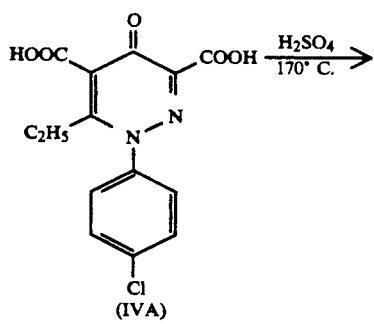

(IVA)

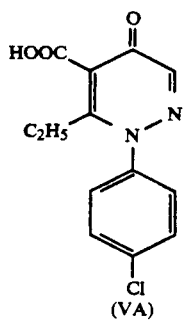

(VA)

Procedure

Compound (IVA) (20.0 g at 96% strength, 0.059 m) was suspended in 98% sulphuric acid (123.3 g) and heated to 170°±2° C., with stirring, for 9 hours. Thin layer chromatography was carried out by adding one drop of the mixture to 2 ml of water in a test-tube, decanting off the supernatant liquor from the precipitate and dissolving the precipitate in acetone (1.0 ml). A spot of the solution was applied to silica gel chromatogram sheet 13181 with fluorescent indicator, and the chromatogram developed in a mixture of ethylacetate/acetone/water (12:11:3). After drying the chromatogram was viewed under ultra violet light. Virtually no (IVA) was detectable near the baseline of the chromatogram and a major band of (VA) could be seen together with a small amount of the twice decarboxylated product at a higher Rf.

The acid solution was then cooled to 25°-30° C. and poured into ice/water (200 ml) with stirring allowing the temperature to rise no higher than 40° C. The product was filtered off then suspended in isopropanol (53 ml) and boiled for 1 hour. The suspension was then cooled to 25° C. and filtered. The filter cake was washed with isopropanol (7 ml). This extraction was repeated once more, and the final product dried overnight at 60° C.

Weight of desired product (VA) = 12.4 g at 99% strength by HPLC
= 12.3 g at 100% strength
= 74.2% theory yield.

EXAMPLES 2-6

Example 1 was repeated, using different concentrations of sulphuric acid in different preparations, as well as different reaction times. Results are shown in Table I below. It will be seen that Examples according to the invention give better yields and product purity than is obtained in the comparative experiments A, B and C.

TABLE I

| Example No. | (I) gm | $H_2SO_4$ gm | $H_2SO$ Strength | Temp. °C. | Reaction Time, Hrs | Product Purity % | % Yield at 100% str. |
|---|---|---|---|---|---|---|---|
| A | 10 | 19.7 | 98% | 140-150 | 18 | 80 | 28.7 |
| B | 10 | 19.7 | 100% | 140-150 | 18 | 55 | 24.8 |
| C | 10 | 19.7 | 98% | 165-170 | 16 | 80 | 50 |
| 2 | 10 | 39.2 | 100% | 170 | 6 | 82.7 | 52.1 |
| 3 | 10 | 39.2 | 100% | 170 | 8 | 98.7 | 54.3 |
| 4 | 10 | 61.6 | 100% | 170 | 7 | 98.7 | 47.4 |
| 5 | 10 | 61.6 | 98% | 170 | 7 | 100 | 70 |
| 6 | 10 | 61.6 | 98% | 170 | 9 | 99 | 74.2 |

We claim:

1. Process for recovering a monocarboxylic acid of formula (V):

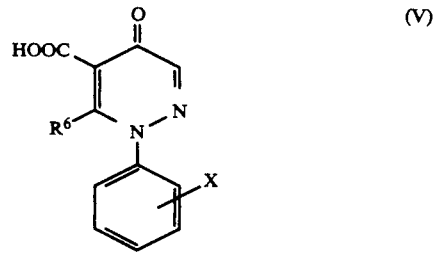

from a dicarboxylic acid of formula (IV):

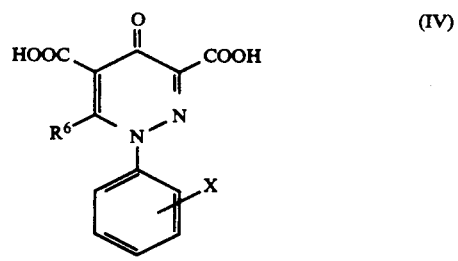

where $R^6$ is H, alkyl or halo, and X represents hydrogen or from one to three substituents (which may be the same or different) selected from alkyl, halo or nitro; which comprises heating the compound (IV) at a temperature in the range 160°-180° C. with 95-100% sulphuric acid for a time sufficient to bring about substantial monodecarboxylation, the weight ratio of (IV) to sulphuric acid used being in the range from about 1:4 to about 1:10.

2. Process as claimed in claim 1 which uses sulphuric acid of about 98% concentration.

3. Process as claimed in claims 1 or 2 which uses a reactant: acid weight ratio of between 1:5 and 1:8.

4. Process as claimed in any of claims 1-3 wherein $R^6$ is $C_1$-$C_6$ alkyl and X is monochloro.

* * * * *